(12) United States Patent
Sakai et al.

(10) Patent No.: US 12,232,988 B2
(45) Date of Patent: Feb. 25, 2025

(54) MEDICAL STENT AND STENT DELIVERY DEVICE

(71) Applicant: OLYMPUS CORPORATION, Hachioji (JP)

(72) Inventors: Ryosuke Sakai, Sagamihara (JP); Toshihiro Yamagata, Hachioji (JP); Kazuhiro Noda, Ebina (JP); Yuko Kirino, Tachikawa (JP); Nozomu Kotake, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 902 days.

(21) Appl. No.: 17/323,317

(22) Filed: May 18, 2021

(65) Prior Publication Data
US 2021/0267778 A1 Sep. 2, 2021

Related U.S. Application Data (63) Continuation of application No. PCT/JP2018/043175, filed on Nov. 22, 2018.

(51) Int. Cl.
*A61F 2/88* (2006.01)
*A61F 2/966* (2013.01)

(52) U.S. Cl.
CPC .............. *A61F 2/885* (2013.01); *A61F 2/966* (2013.01)

(58) Field of Classification Search
CPC .. A61F 2/885; A61F 2/966; A61F 2/04; A61F 2/82; A61F 2/848;
(Continued)

(56) References Cited

U.S. PATENT DOCUMENTS

| 5,282,860 A | 2/1994 | Matsuno et al. |
| 2007/0293929 A1* | 12/2007 | Aoba .................. A61F 2/95 623/1.11 |

(Continued)

FOREIGN PATENT DOCUMENTS

| EP | 2489334 A1 | 8/2012 |
| EP | 2803339 A1 | 11/2014 |

(Continued)

OTHER PUBLICATIONS

Feb. 19, 2019 International Search Report issued in International Patent Application No. PCT/JP2018/043175.

(Continued)

*Primary Examiner* — Bruce E Snow
(74) *Attorney, Agent, or Firm* — Oliff PLC (57) ABSTRACT

A medical stent including: a tubular main body made of resin that extends along an axis; a first locking member including a first fixed end fixed to the distal end side of the main body, and a first free end positioned radially outward of the main body; a second locking member including a second fixed end fixed to the proximal end side of the main body, and a second free end positioned radially outward of the main body; and a spiral reinforcing material made of metal which is embedded between the inner and outer circumferential surfaces of the main body. The reinforcing material includes a first portion spirally wound between the first and second fixed ends, a second portion spirally wound at a pitch greater than that of the first portion, and a third portion spirally wound at a pitch greater than that of the second portion.

17 Claims, 9 Drawing Sheets

(58) Field of Classification Search
CPC . A61F 2002/8486; A61F 2/95; A61M 31/007; A61M 37/0069; A61N 5/1027
See application file for complete search history.

(56) References Cited

U.S. PATENT DOCUMENTS

| | | |
|---|---|---|
| 2010/0160847 A1 | 6/2010 | Braido et al. |
| 2012/0101562 A1* | 4/2012 | Gunderson ............. A61F 2/966 623/1.12 |
| 2014/0114431 A1* | 4/2014 | Yamagata ................. A61F 2/04 623/23.7 |
| 2014/0288496 A1* | 9/2014 | Miyoshi ................... A61B 1/07 604/95.01 |
| 2015/0005894 A1* | 1/2015 | Nomura .................... A61F 2/04 623/23.7 |
| 2016/0100962 A1* | 4/2016 | Yanuma .................... A61F 2/94 623/23.7 |
| 2016/0100965 A1 | 4/2016 | Nishigishi |

FOREIGN PATENT DOCUMENTS

| | | |
|---|---|---|
| EP | 2965723 A1 | 1/2016 |
| JP | 2016-073553 A | 5/2016 |
| WO | 2011/118081 A1 | 9/2011 |
| WO | 2014/136334 A1 | 9/2014 |

OTHER PUBLICATIONS

Sep. 4, 2024 Office Action issued in German Patent Application No. 11 2018 008 164.8.

* cited by examiner

MEDICAL STENT AND STENT DELIVERY DEVICE

CROSS REFERENCE TO RELATED APPLICATIONS

This application is a continuation application based on a PCT Patent Application No. PCT/JP2018/043175, filed on Nov. 22, 2018, the entire content of which is hereby incorporated by reference.

TECHNICAL FIELD

The present disclosure relates to a medical stent and a stent delivery device using the medical stent.

BACKGROUND

A stent is known to be placed in the bile duct as a treatment for bile duct stenosis. It may be necessary to replace the stent due to blockage of the indwelling stent.

When replacing a stent, the indwelling stent is first removed and recovered.

As one of the methods for recovering a stent, a method for recovering the removed stent through an endoscopic treatment tool channel is known.

When collecting the stent through the treatment tool channel, an operator holds the end of the stent with a treatment tool such as grasping forceps or a snare and pulls it into the channel. At this time, the end portion of the stent may be bent and overlapped at the held portion. Overlapping ends of the stent increase the radial dimension, so the overlapping ends must be crushed radially in order to pull the stent into the channel.

The stent described above can be made of a resin and a coil. Since no coil is arranged at the end of this stent, it is easily crushed in the radial direction. As a result, it can be smoothly drawn into the channel and collected.

SUMMARY

The stent described above has a region where a coil is not arranged and a region where a coil is arranged. When this stent is placed, if the stent is pushed in to breach through a place with strong stenosis, stress is concentrated on the boundary between two regions with greatly different rigidity, and buckling is likely to occur. As a result, there is a possibility that the stenosis cannot be breached and the stent cannot be placed, or even if the stent can be placed, the lumen of the buckling site becomes narrow and replacement is required early after the placement.

Based on the above circumstances, it is an object of the present disclosure to provide a stent that does not easily buckle during indwelling and whose ends are easily crushed during recovery.

A first aspect of the present disclosure is a medical stent including: a resin main body formed in a tubular shape along a longitudinal axis between the distal end and the proximal end thereof; a first locking member including a first fixed end fixed to a distal end side of the main body and a first free end positioned outward of an outer circumferential surface of the main body in a radial direction of the main body; a second locking member having a second fixed end fixed to a proximal end side of the main body and a second free end positioned outward of the outer circumferential surface of the main body in the radial direction of the main body; and a reinforcing material made of metal that extends spirally around the longitudinal axis of the main body and is embedded between an inner circumferential surface of the main body and the outer circumferential surface of the main body.

The reinforcing material includes a first portion spirally wound at a position between the first fixed end and the second fixed end, a second portion spirally wound at a pitch larger than a pitch of the first portion, and a third portion spirally wound at a pitch larger than the pitch of the second portion.

A second aspect of the present disclosure is a stent delivery device including: a guide catheter including a guide tube through which a guide wire can be inserted and a wire connected to the guide tube; a pusher catheter including a first tube having a first lumen through which the wire can be inserted, and a second tube having a second lumen connected to a distal end of the first lumen and through which the guide tube can be inserted; and a connecting member including a loop that is connected to a distal end of the pusher catheter. The medical stent is designed to be attached to an outer circumferential surface of the guide tube and positioned distal to a distal end of the second tube.

The main body of the stent has a through hole that opens on the outer circumferential surface between the proximal end and the second fixed end. The stent is designed to be positioned with respect to the pusher catheter by inserting the guide tube into the loop of the connecting member in a state in which the loop is inserted into the through hole in the main body of the stent.

DETAILED DESCRIPTION OF EMBODIMENTS

An exemplary embodiment of the present disclosure will be described with reference to FIGS. 1 to 7.

Figure 1:
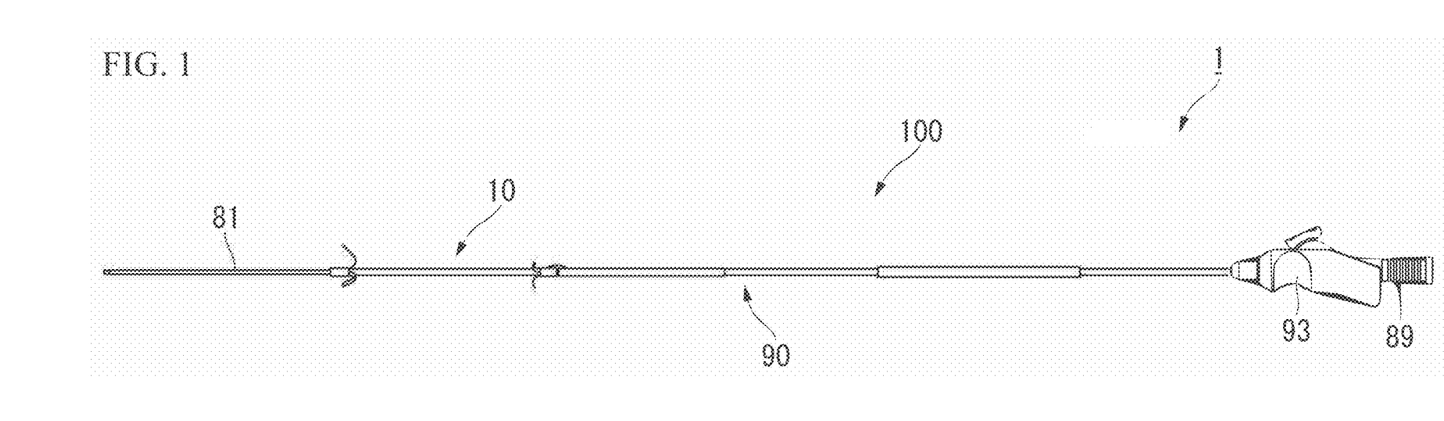
FIG. 1 is an overall view of a stent delivery device according to an exemplary embodiment of the present disclosure.

FIG. 1 is an overall view of a stent delivery device 1 of the present embodiment. The stent delivery device includes a medical stent (hereinafter, simply referred to as "stent") 10 and a delivery catheter 100.

Figure 2:
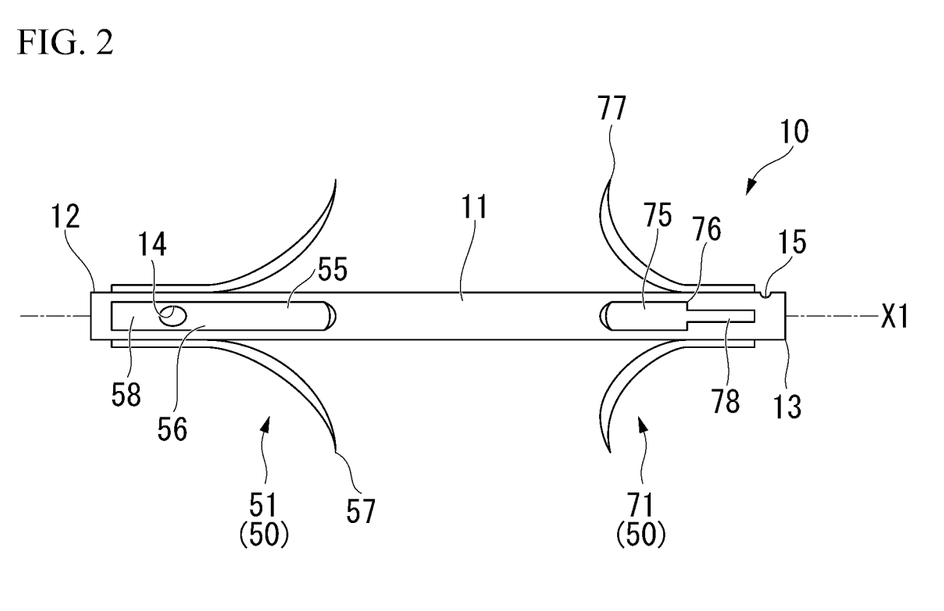
FIG. 2 is a side view of a stent according to the exemplary embodiment.

FIG. 2 is a side view of the stent 10. The stent 10 of the present embodiment is a stent placed in the bile duct, and includes a tubular main body 11 and flaps 50 attached to both ends of the main body 11. The main body has a distal end 12 and a proximal end 13 and extends along the longitudinal axis X1. The distal end 12 is an end portion that is placed on the liver side when placed in the bile duct. The proximal end 13 is an end that is placed on the duodenal papilla side when placed in the bile duct.

Figure 3:
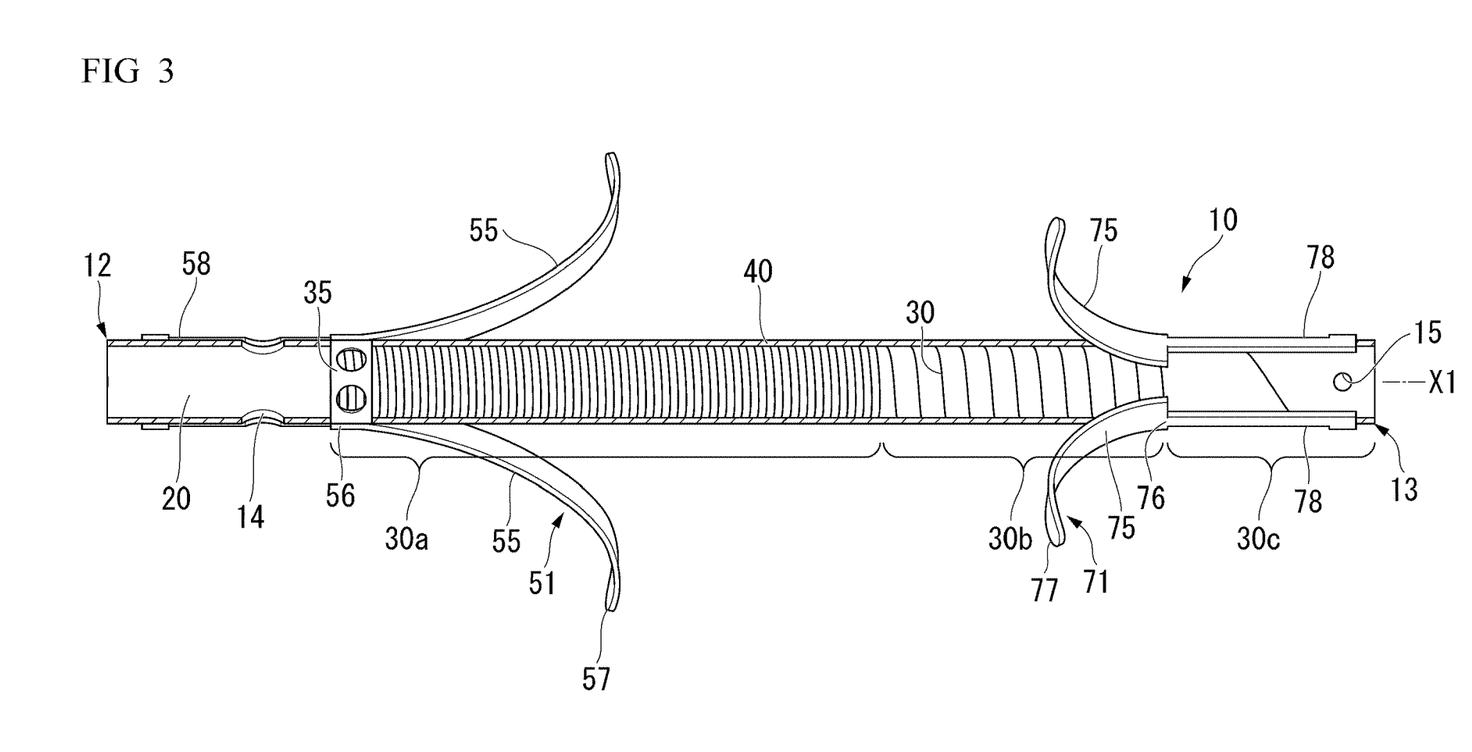
FIG. 3 is a perspective view of the stent.

FIG. 3 is a perspective view of the stent 10 in which the outer layer of the stent 10 is transparently represented. The main body 11 has a resin inner layer 20, a metal wire (reinforcing material) 30 wound around the inner layer 20, and a resin outer layer 40 covering the inner layer 20 and the wire 30. The wire 30 is embedded between the inner circumferential surface and the outer circumferential surface of the main body 11.

The inner layer 20 is a tube formed of a resin material having a smooth surface and biocompatibility, such as PTFE (polytetrafluoroethylene) and PFA (perfluoroalkoxy alkane).

The wire 30 is spirally wound on the outer circumferential surface of the inner layer 20, and is formed in a coil shape as a whole. By spirally winding the wire 30 between the inner circumferential surface and the outer circumferential surface of the main body 11, buckling of the stent 10 can be suppressed and the flexibility of the stent 10 is improved. The material of the wire 30 is a material having X-ray impermeability such as tungsten steel and stainless steel. The wire 30 has a plurality of regions having different winding pitches. Details will be described later.

The outer layer 40 is made of a resin material having elasticity, flexibility and biocompatibility such as urethane or polyethylene. The outer layer 40 is also provided in a gap between adjacent wires 30 in the longitudinal axis X1 direction.

The flap 50 has a first flap 51 provided on the distal end 12 side and a second flap 71 provided on the proximal end 13 side.

The first flap 51 has a plurality of first locking members 55. Each first locking member 55 is an elongated member having a first fixed end 56 and a first free end 57 and extending between the first fixed end 56 and the first free end 57.

In each first locking member 55, a rib 58 extends from the first fixed end 56. The width of the rib 58 is the same as that of the first locking member 55. Each first locking member 55 is attached to the main body 11 by joining the rib 58 to the outer circumferential surface of the main body 11. The ribs 58 can be joined by heat fusion, adhesion, or the like. By joining the rib 58 to the main body 11, the first fixed end 56 of each first locking member 55 is fixed to the main body 11. The first locking member 55 extends from the first fixed end 56 toward the first free end 57 in a direction gradually away from the proximal end 13 side of the main body 11 and the outer circumferential surface of the main body 11.

The second flap 71 has a structure similar to that of the first flap 51, and has a plurality of second locking members 75. Here, the second locking member 75 is shorter than the first locking member 55. Each second locking member 75 has a second fixed end 76 and a second free end 77. The rib 78 extends from the second fixed end 76. Each second locking member 75 is attached to the main body 11 by joining the rib 78 to the outer circumferential surface of the main body 11, and the second fixed end 76 is fixed to the main body 11. The second locking member 75 extends from the second fixed end 76 toward the second free end 77 in a direction gradually away from the distal end 12 side of the main body 11 and the outer circumferential surface of the main body 11.

The number of the first locking members 55 in the first flap 51 and the number of the second locking members 75 in the second flap 71 can be appropriately set. In this embodiment, the first flap 51 and the second flap 71 each have four locking members. The four locking members 55 are attached at equal intervals in the circumferential direction of the main body 11.

In the first flap 51 and the second flap 71, the phases on the outer circumferential surface of the main body 11 to which the locking member is attached may be the same or different. In the first flap 51 and the second flap 71, the number of locking members may be the same or different.

The spirally wound wire 30 is attached between the first fixed end 56 and the proximal end 13. The end of the wire 30 on the distal end side is fixed to the main body by a metal ring 35. The wire 30 has a plurality of regions having different winding pitches in the longitudinal axis X1 direction. The winding pitch in each region is generally uniform. The first region (first portion) 30a on the most distal side is positioned at least between the first fixed end 56 and the second fixed end 76, and has the smallest winding pitch. The winding pitch of the second region (second portion) 30b adjacent to the first region 30a is larger than the winding pitch of the first region 30a. The winding pitch of the third region (third portion) 30c adjacent to the second region 30b and positioned closest to the proximal end side is larger than the winding pitch of the second region 30b.

The winding number per unit length of the wire 30 is largest in the first region 30a, less in the second region 30b than in the first region 30a, and least in the third region 30c. The value of the winding angle (inclination) of the wire 30 with respect to the longitudinal axis X1 is the closest to the right angle in the first region 30a and the largest difference from the right angle in the third region 30c. The value of the winding angle of the second region 30b is intermediate between the first region 30a and the third region 30c.

The boundary between the first region 30a and the second region 30b is positioned between the first fixed end 56 and the second fixed end 76 and between the first free end 57 and the second free end 77 in the longitudinal axis X1 direction. The boundary between the second region 30b and the third region 30c is substantially the same as the position of the second fixed end 76 in the longitudinal axis X1 direction. In the longitudinal axis X1 direction, the second region 30b is longer than the third region 30c.

The length of the second locking member 75, that is, the length from the second fixed end 76 to the second free end 77 is shorter than the length of the second region 30b in the longitudinal axis X1 direction.

In the main body 11, a through hole 14 communicating with the internal space of the main body 11 is formed on the outer circumferential surface between the first fixed end 56 and the distal end 12, and bile can flow in from the outer circumferential surface side of the main body 11. The number and position of the through holes 14 can be appropriately set. Some or all of the through holes 14 may overlap the rib 58.

A through hole 15 communicating with the internal space of the main body 11 is formed on the outer circumferential surface of the third region 30c. The position of the through hole 15 can be set as appropriate. Some or all of the through holes 15 may overlap the rib 78.

Figure 4:
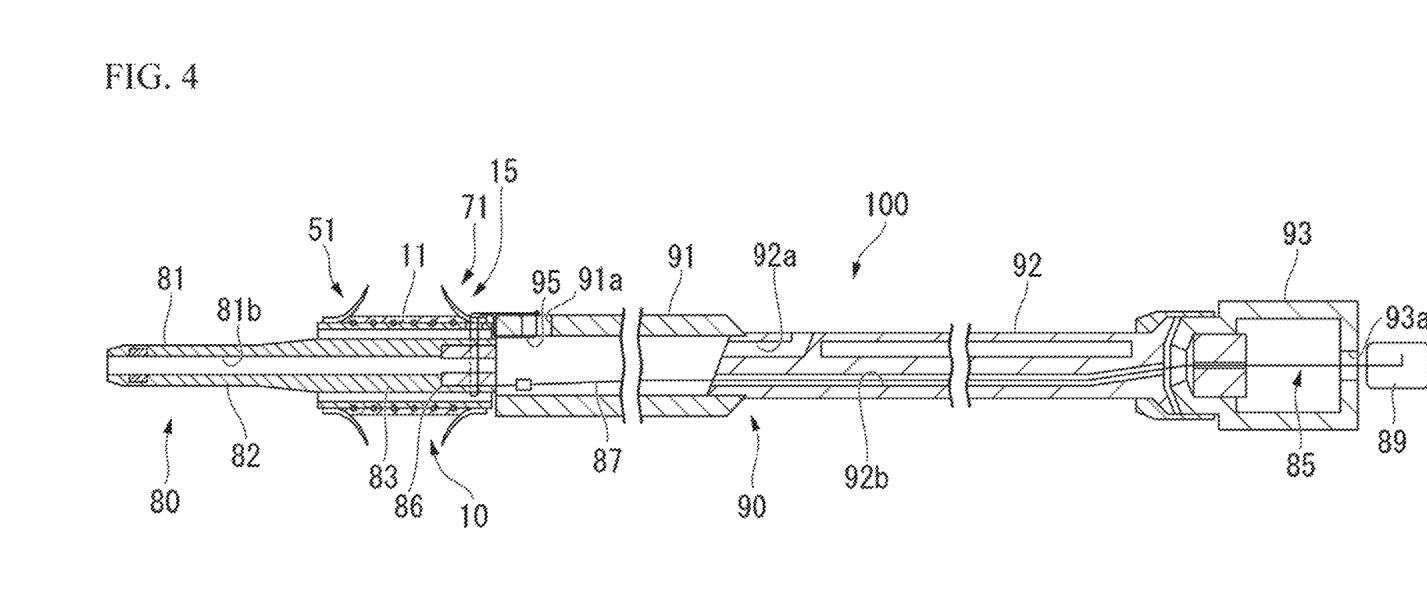
FIG. 4 is a schematic cross-sectional view of the stent delivery device.

FIG. 4 is a schematic cross-sectional view showing the structure of the stent delivery device 1. The delivery catheter 100 includes a guide catheter 80 and a pusher catheter 90.

The guide catheter 80 has a tube (guide tube) 81 through which a guide wire can be inserted, and a traction portion 85 for moving the tube 81.

The tube 81 is a tubular member made of resin and has a cavity through which a guide wire can be inserted. The tube 81 is flexible enough to be deformed when the tube 81 comes into contact with a living tissue when the delivery device 1 is used. The tube 81 is an elastic member having a restoring force, and becomes linear due to the restoring force in a state where no external force is applied. The inner circumferential surface 81b of the tube 81 is circular in the radial cross-sectional view of the tube 81. The tube 81 has a small diameter portion 82 positioned on the distal end side of the delivery device 1 and a large diameter portion 83 positioned on the proximal end side of the delivery device 1. The outer circumferential surface of the small diameter portion 82 and the outer circumferential surface of the large diameter portion 83 are connected by a smooth curved surface. As a result, the outer diameter of the tube 81 gradually increases from the small diameter portion 82 toward the large diameter portion 83.

The outer diameters of the small diameter portion 82 and the large diameter portion 83 are smaller than the inner diameter of the stent 10. Therefore, by inserting the tube 81 into the stent 10, the stent 10 can be attached to the tube 81.

When the diameter of the stent 10 is small or the like, the tube 81 may not have a small diameter portion and a large diameter portion and may have the same diameter in the longitudinal direction.

The traction portion 85 includes a pipe 86, a wire 87, and an operation portion 89. The pipe 86 is a metal tubular member having both ends open in the axial direction. The pipe 86 is coaxial with the tube 81 and is embedded in the wall of the tube 81. The pipe 86 is arranged at the proximal end portion of the large diameter portion 83.

The wire 87 is made of metal, the distal end thereof is welded to the pipe 86, and the proximal end portion is connected to the operation portion 89.

The pusher catheter 90 has a single lumen tube (second tube) 91, a multi-lumen tube (first tube) 92, and a grip portion 93.

The single lumen tube 91 is a tubular member having an inner diameter through which the large diameter portion 83 of the tube 81 can enter. The single lumen tube 91 has flexibility. The distal end surface of the single lumen tube 91 is a plane orthogonal to the center line of the single lumen tube 91. The distal end surface of the single lumen tube 91 contacts the proximal end of the stent 10 to support the stent 10. The size of the wall thickness of the single lumen tube 91 is equal to or larger than the difference between the inner radius and the outer radius of the main body 11 of the stent 10 (that is, the wall thickness of the stent 10). The single lumen tube 91 has a length that allows the large diameter portion 83 of the tube 81 to be completely accommodated inside the single lumen tube 91. The material of the single lumen tube 91 is not particularly limited, but a resin is preferable.

The multi-lumen tube 92 is fixed to the proximal end of the single lumen tube 91. The multi-lumen tube 92 has a guide wire lumen 92a for inserting the guide wire and a wire lumen (first lumen) 92b. The wire 87 of the guide catheter 80 is inserted through the wire lumen 92b.

The guide wire lumen 92a is open to the distal end of the multi-lumen tube 92 and is open to the side surface of the multi-lumen tube 92 on the proximal end side of the distal end of the multi-lumen tube 92.

The wire lumen 92b is open at the distal end and proximal end of the multi-lumen tube 92.

The grip portion 93 is connected to the proximal end of the multi-lumen tube 92. The grip portion 93 has a substantially cylindrical shape having a diameter larger than that of the multi-lumen tube 22. The outer circumferential surface of the grip portion 93 may be formed with irregularities or the like to prevent slipping.

The grip portion 93 is formed with a through hole 93a that communicates with the wire lumen 92b. The through hole 93a is positioned on an extension line toward the proximal end side of the center line of the multi-lumen tube 92.

The wire 87 of the guide catheter 80 is inserted through the through hole 93a. As a result, the wire 87 and the operating portion 89 extend from the through hole 93a.

A hole 91a communicating with the internal space is provided at the distal end of the single lumen tube 91. A thread (connecting member) 95 is passed through the hole 91a. The end of the thread 95 is tied to form a loop. The looped thread 95 enters the main body 11 of the stent 10 through the through hole 15. The tube 81 of the guide catheter 80 passes through the loop of the thread 95 within the stent 10.

The operation when the stent delivery device 1 configured as described above is used will be described.

The operator passes the guide wire through the channel of the side-viewing endoscope and inserts the guide wire into the bile duct while observing with the endoscope. The operator then operates the guide wire under fluoroscopy to breach through the stenotic site in the bile duct and move the distal end of the guide wire deeper than the stenotic site.

The operator inserts the proximal end of the guide wire protruding from the forceps opening of the endoscope into the distal end opening of the tube 81 of the stent delivery device 1 to which the stent 10 is mounted. The guide wire enters the lumen of the single lumen tube 91 through the proximal opening of the tube 81. Further, the operator causes the proximal end portion of the guide wire to enter the guide wire lumen 92a and protrude from the proximal end side opening of the guide wire lumen 92a.

The operator inserts the stent delivery device 1 through which the guide wire is passed into the channel of the endoscope, and protrudes the distal end of the stent delivery device 1 from the distal end of the channel. The operator operates a rising base of the endoscope to direct the distal end of the stent delivery device 1 toward the duodenal papilla and allow the stent delivery device 1 to enter the bile duct along the guide wire.

Figure 5:
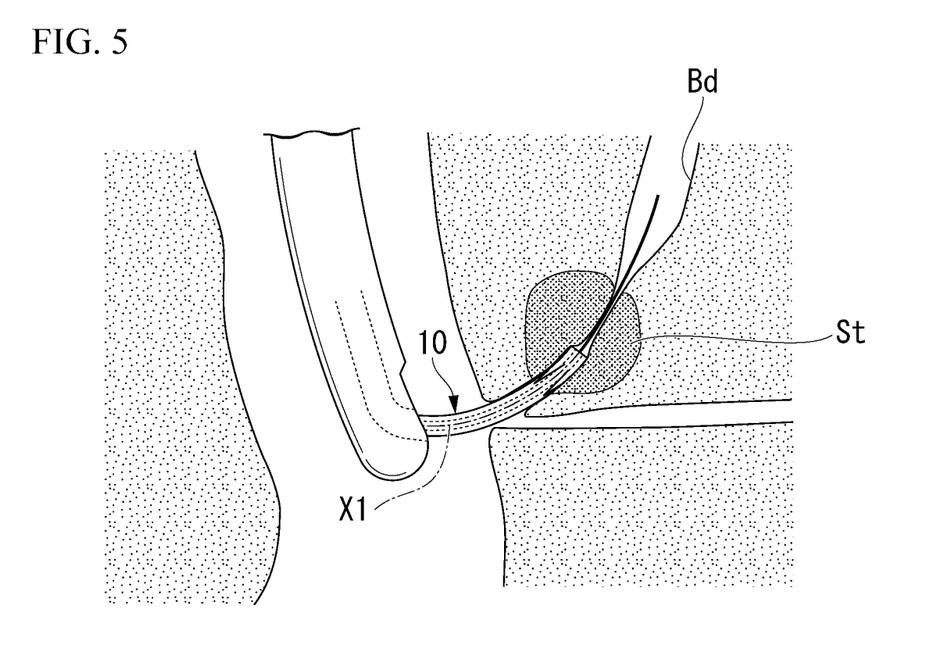
FIG. 5 is a diagram showing a process of placing a stent using the stent delivery device.

As shown in FIG. 5, when the distal end of the stent delivery device 1 approaches the stenotic site St in the bile duct Bd, insertion resistance occurs. Due to such insertion resistance, a compressing force acts on the stent 10 in the longitudinal axis X1 direction. This force is concentrated on the site of the stent 10 where the structure changes significantly.

In the stent 10, since the wire 30 has the first region 30a, the second region 30b, and the third region 30c, the above-described force acts in a dispersed manner at the boundary between the first region 30a and the second region 30b and at the boundary between the second region 30b and the third region 30c. As a result, buckling during placement of the stent 10 is preferably prevented.

In the stent 10, the rib 78 joined to the third region 30c extends parallel to the longitudinal axis X1 of the stent 10. The rib 78 exerts a bone-like function in the third region 30c and enhances the above-described buckling prevention effect.

Since the width of the rib 78 is smaller than the width of the second locking member 75, the volume per unit length of the rib 78 is smaller than that of the second locking member 75. As a result, the third region 30c is prevented from becoming too hard and the insertability and the followability to running of the bile duct are prevented from being reduced.

When the first flap 51 moves deeper than the stenosis site St, the operator advances and retracts the stent delivery device 1 to determine the placement position of the stent 10. In the stent delivery device 1, as long as the tube 81 passes through the loop of the thread 95, the stent 10 does not come off the pusher catheter 90. Therefore, the stent 10 can be pulled back by retracting the stent delivery device 1. As such, the position of the stent 10 can be easily adjusted.

Figure 6:
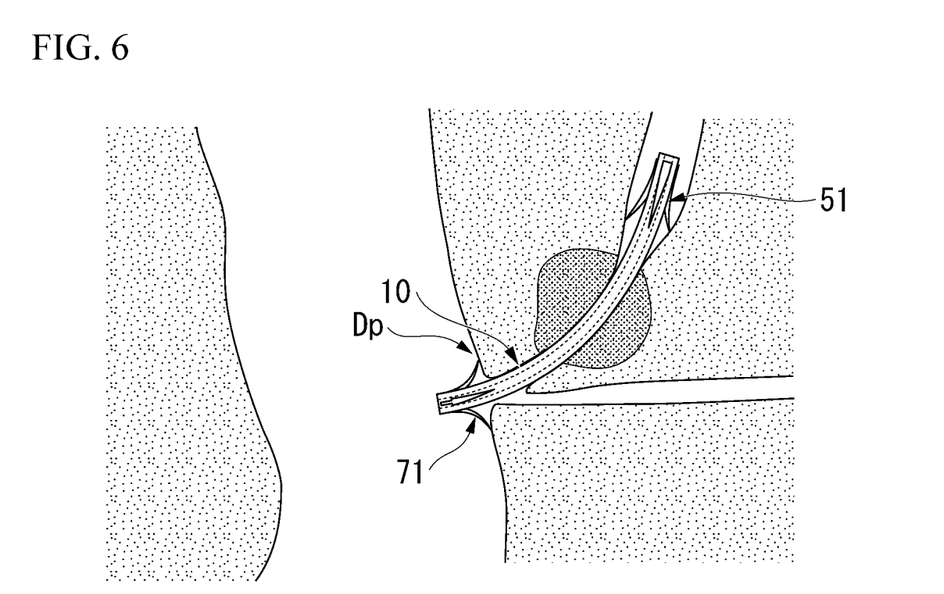
FIG. 6 shows an indwelling stent.

After determining the placement position of the stent 10, the operator pulls the operation portion 89 toward the hand while holding the pusher catheter 90. Then, the wire 87 and the tube 81 retract, but the stent 10 does not retract because it is in contact with the pusher catheter 90. When the tube 81 retracts and comes out of the stent 10 and the thread 95, the thread 95 disengages the stent 10 from the pusher catheter 90 and the stent 10 is placed in a desired position within the bile duct, as shown in FIG. 6.

After placement of the stent 10, the first flap 51 is placed on the back side of the stenosis site St, and the second flap 71 is placed near the duodenal papilla Dp outside the bile duct, so that the placement position is preferably held.

Next, the operation when the indwelling stent is collected via the endoscopic channel will be described.

The operator introduces a lateral endoscope to the vicinity of the duodenal papilla and protrudes a recovery tool such as grasping forceps or a snare from the channel. Next, the operator holds the proximal end of the stent 10 by the recovery tool.

Figure 7:
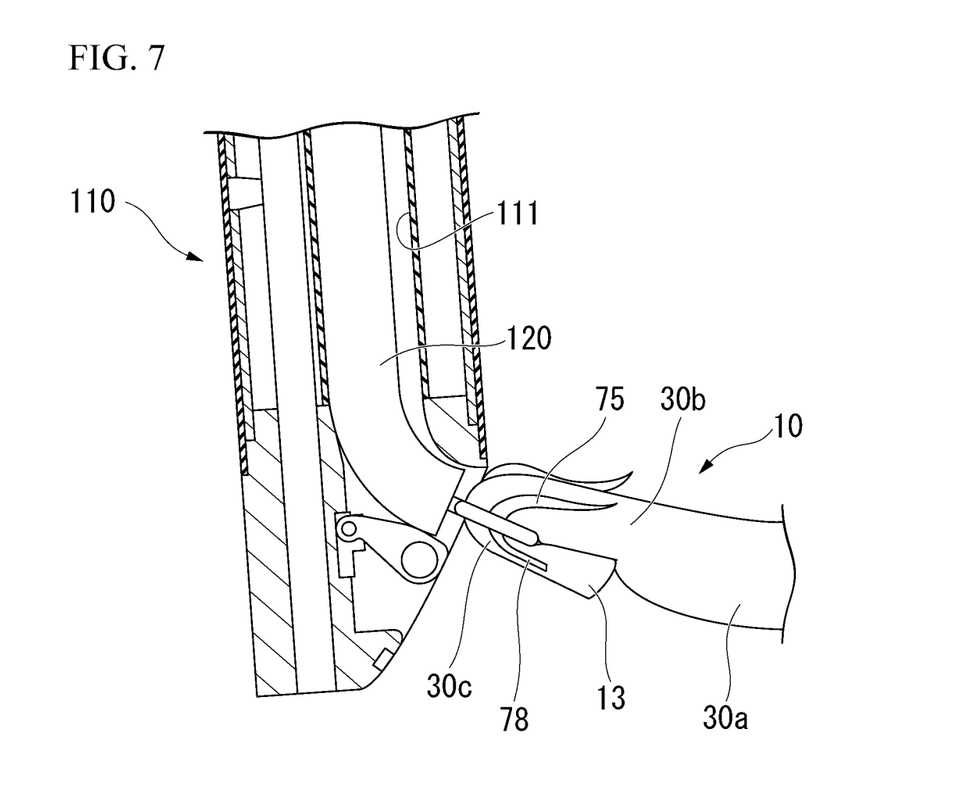
FIG. 7 shows a process of pulling the stent into an endoscope channel.

The operator retracts the recovery tool holding the stent 10. When the stent 10 reaches the channel distal end opening of the side endoscope, the stent 10 is pulled into a channel 111 of the endoscope 110 while being folded back at the site held by the recovery tool 120, as shown in FIG. 7. Since the portion (holding portion) held by the collector 120 is the third region 30c or the second region 30b, and the region to be folded back is a region closer to the proximal end 13 than the holding portion, the region to be folded back always becomes the third region 30c or the second region 30b, and the first region 30a is not folded back. That is, when the stent 10 of the present embodiment is recovered via the channel of the endoscope, the third region 30c or the second region 30b, each of which has a larger winding pitch of the wire 30 than the first region 30a, is folded back and is easily crushed, and the stent 10 is easily crushed and retracted into the channel 111. As described above, since the volume per unit length of the rib 78 is smaller than that of the second locking member 75, the rib 78 is less likely to prevent the third region 30c from being crushed.

In order to ensure that the stent 10 operates as described above at the time of recovery, it is necessary to place either the second region 30b or the third region 30c in the entire region on the proximal end side of the position closest to the distal end of the range that can be held by the recovery tool 120 in the stent 10. As long as this condition is satisfied, the arrangement order and length of the second region and the third region may be appropriately set.

Another exemplary embodiment of the present disclosure will be described with reference to FIG. 8. In the following description, the same reference numerals will be given to the configurations common to those already described, and duplicate description will be omitted.

Figure 8:
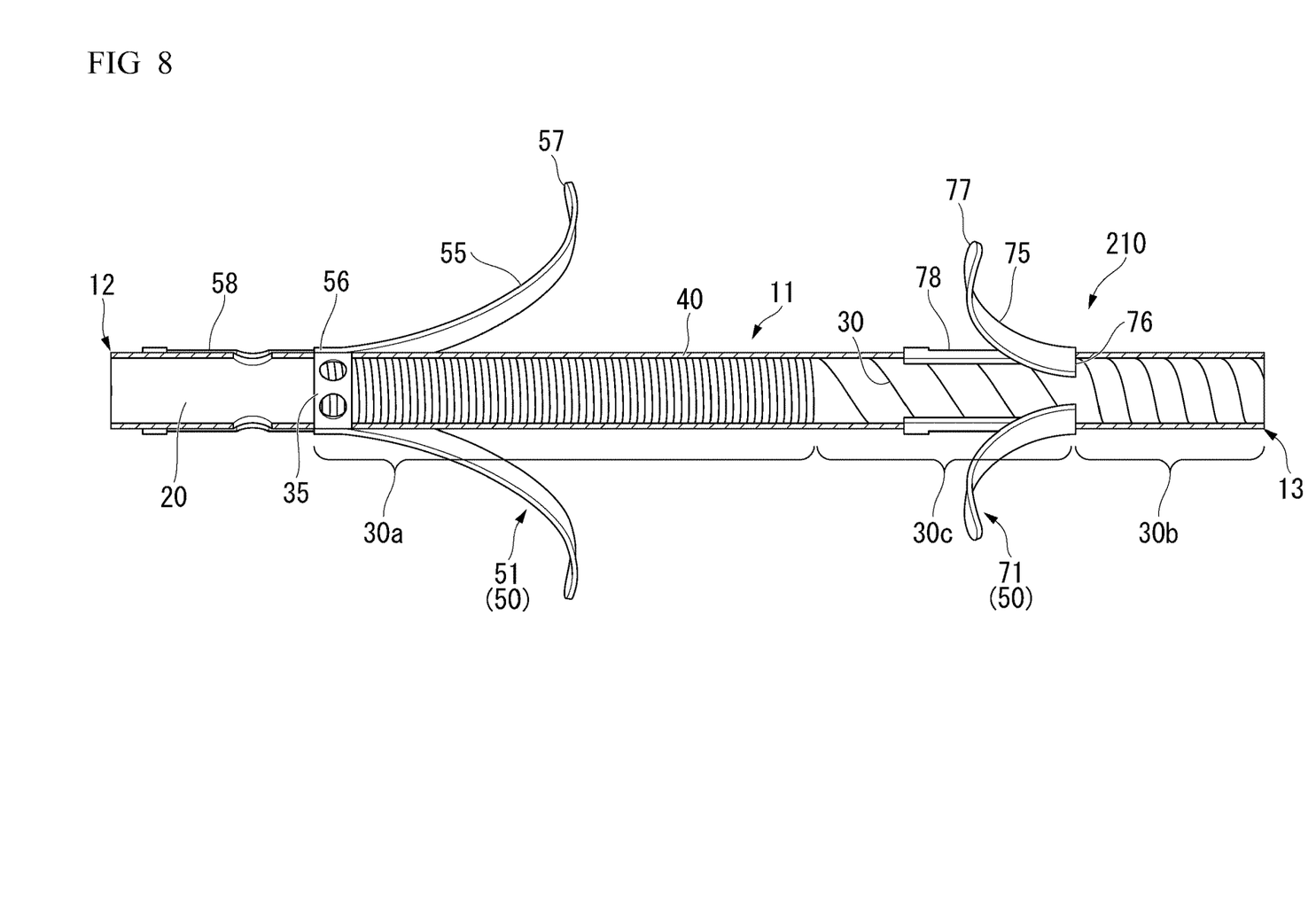
FIG. 8 is a schematic view showing a structure of a stent according to an exemplary embodiment of the present disclosure.

FIG. 8 is a diagram schematically showing the structure of the stent 210 of the present embodiment. In the stent 210, the winding pitch of the wire 30 is set so that the first region 30a, the third region 30c, and the second region 30b are positioned in this order from the distal end side.

The second fixed end 76 of the second locking member 75 is positioned at the proximal end of the third region 30c. The rib 78 extends from the proximal end portion of the third region 30c toward the distal end portion and is joined to the third region 30c. That is, the rib 78 is connected to the second fixed end 76 of the second locking member 75, and the rib 78 extends from the second fixed end 76 toward the distal end 12 side.

Although the stent 210 of the present embodiment has a different structure from that of the stent 10 of the above embodiment, it has substantially the same effect. That is, since the third region 30c having the largest winding pitch is appropriately reinforced by the rib 78, the third region 30c exhibits a good balance between buckling resistance and crushability at the time of collection.

Although each embodiment of the present disclosure has been described above, the technical scope is not limited to the above-described embodiments, and it is possible to change the combination of components, make various changes to each component, and omit them without departing from the spirit of the present disclosure.

Some changes are shown below, but not all, and other changes are possible. Two or more of these changes may be combined as appropriate.

Figure 9:
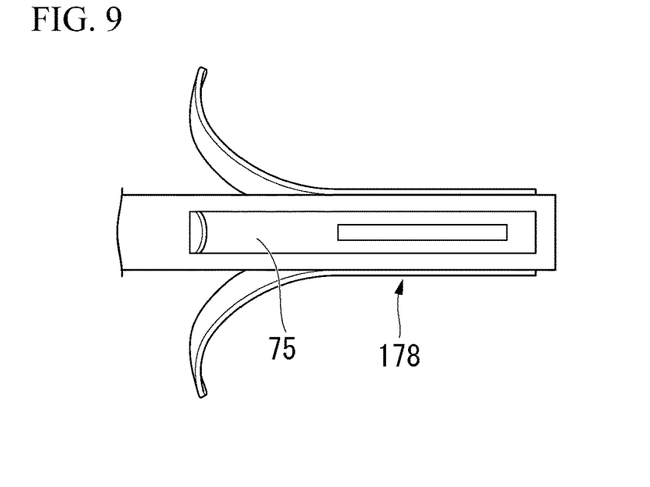
FIG. 9 is a diagram showing an example of the rib.
Figure 10:
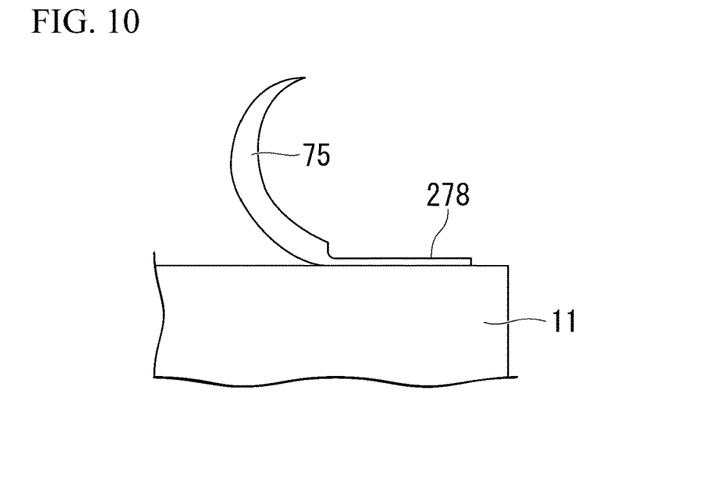
FIG. 10 is a diagram showing an example of the rib.

The shape of the rib of the second locking member is not limited to the narrow shape described above. For example, as in the rib 178 shown in FIG. 9, even if the width is the same as that of the second locking member 75 and the inside is partially hollowed out, the volume per unit length can be made smaller than that of the second locking member. By forming the rib 278 thinner than the second locking member 75, as shown in FIG. 10, the volume per unit length can be made smaller than that of the second locking member.

Figure 11:
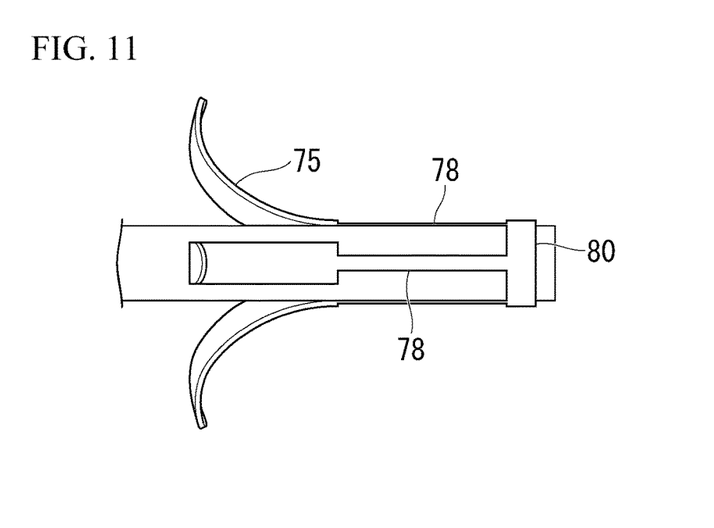
FIG. 11 is a diagram showing an example of the rib.

As shown in FIG. 11, a plurality of ribs 78 may be connected by an annular connecting portion 80 extending in the circumferential direction of the main body 11. In this way, the plurality of second locking members can be attached while maintaining the positional relationship in the circumferential direction of the main body. This structure may be applied to the first flap.

By providing a resin layer so as to cover the ribs, the joint between the ribs and the main body may be strengthened.

Since the distal end side of the stent does not need to be crushed at the time of recovery, the shape of the rib of the first locking member does not necessarily have to be the same as that of the second locking member.

If the stent is not attached to the delivery catheter in advance, it may have a structure that does not have a through hole 15.

Figure 12:
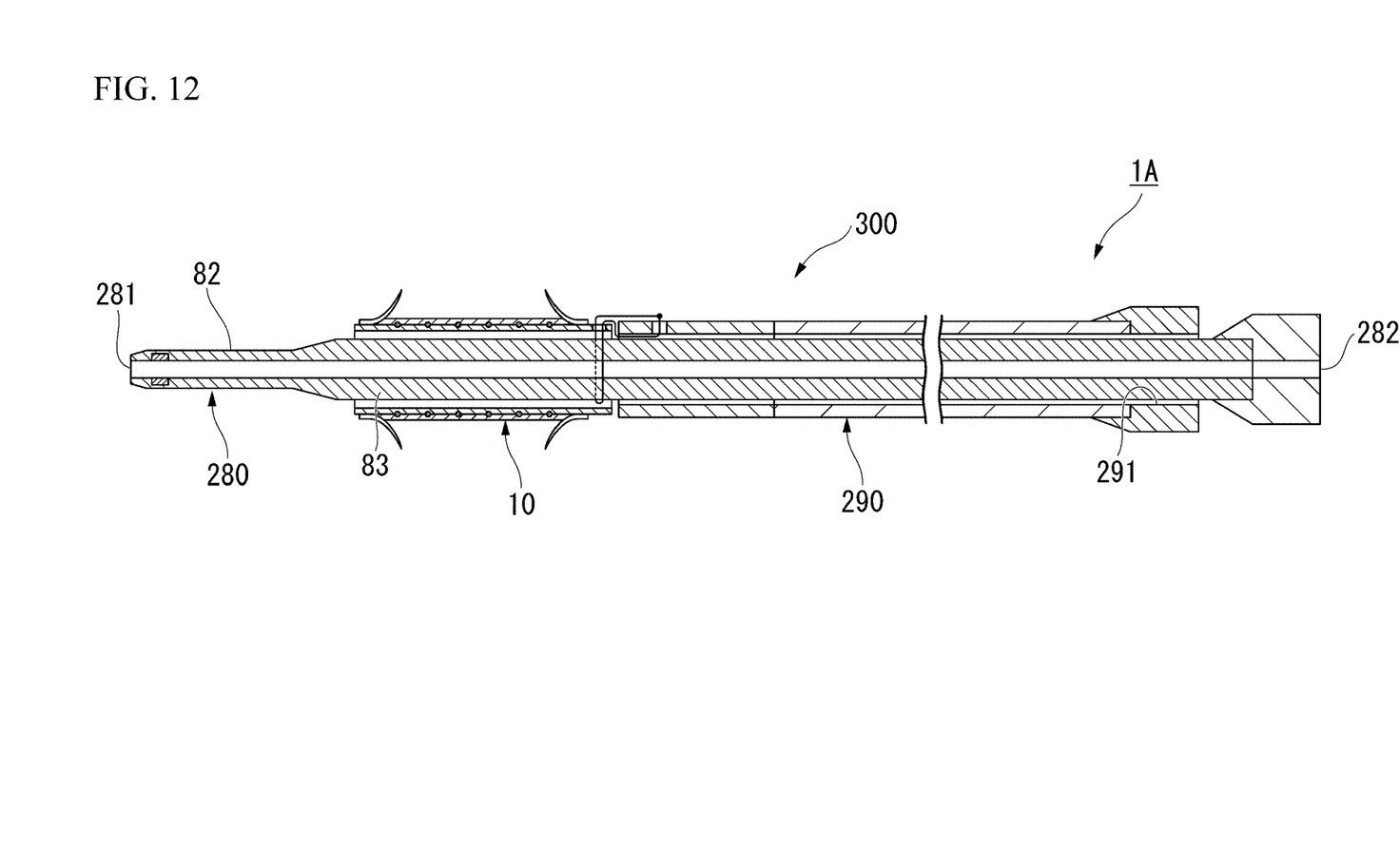
FIG. 12 is a schematic cross-sectional view of a stent delivery device according to an exemplary embodiment of the present disclosure.

The delivery catheter is not limited to that having the above-described structure. FIG. 12 shows another configuration example of the stent delivery device. The delivery catheter 300 of the stent delivery device 1A shown in FIG. 12 includes a guide catheter 280 and a pusher catheter 290. The pusher catheter 290 is composed of only a single lumen tube and does not have a multi-lumen tube. The guide catheter 280 has a small diameter portion 82 and a large diameter portion 83, and does not have a traction portion. The large diameter portion 83 extends within the pusher catheter 290 and protrudes from the proximal opening 291 of the pusher catheter 290.

In the stent delivery device 1A, the guide wire that has entered from the distal end opening 281 of the guide catheter 280 passes through the guide catheter 280 and protrudes from the proximal opening 282. The stent delivery device 1A requires a guide wire longer than that of the stent delivery device 1, but has the same effect as the stent delivery device 1.

The present disclosure can be applied to stents and stent delivery devices.

What is claimed is:

1. A medical stent comprising:
a resin main body that includes a distal end and a proximal end and is formed in a tubular shape along a longitudinal axis between the distal end and the proximal end;
a flap including a fixed end fixed to a proximal end side of the main body and a free end positioned outward of an outer circumferential surface of the main body in a radial direction of the main body, the flap extending from the fixed end to the free end;
a rib that extends along the longitudinal axis and is connected to the fixed end; and
a reinforcing material made of metal that extends spirally around the longitudinal axis of the main body between the distal end and the proximal end of the main body and is embedded between an inner circumferential surface of the main body and the outer circumferential surface of the main body,
wherein:
the reinforcing material includes
a first portion that is spirally wound,
a second portion spirally wound at a pitch larger than a pitch of the first portion, and
a third portion spirally wound at a pitch larger than the pitch of the second portion, the third portion being positioned between the rib and the inner circumferential surface of the main body, and
the rib extends from the fixed end in a direction away from the second portion of the reinforcing material, and is fixed to the outer circumferential surface of the main body along an entirety of a length of the rib along the longitudinal axis.

2. The medical stent according to claim 1, wherein a length of the second portion is longer than a length of the third portion in a direction along the longitudinal axis of the main body.

3. The medical stent according to claim 1, wherein a length from the fixed end to the free end is shorter than a length of the second portion in a direction along the longitudinal axis of the main body.

4. The medical stent according to claim 1, wherein the first portion is positioned distal of the third portion, and the second portion is positioned proximal of the third portion along the longitudinal axis of the main body.

5. The medical stent according to claim 4, wherein the rib extends from the fixed end in a distal direction along the longitudinal axis.

6. The medical stent according to claim 1, wherein the main body further includes a resin inner layer and a resin outer layer, and
the reinforcing material is embedded between the resin inner layer and the resin outer layer.

7. The medical stent according to claim 1, further comprising:
a second flap including a second fixed end fixed to a distal end side of the main body and a second free end positioned outward of the outer circumferential surface of the main body in the radial direction of the main body, the second flap extending from the second fixed end to the second free end; and
a second rib that extends from the second fixed end along the longitudinal axis.

8. The medical stent according to claim 1, wherein:
a pitch of the first portion is substantially uniform; and
a pitch of the second portion is substantially uniform.

9. A medical stent comprising:
a resin main body that includes a distal end and a proximal end and is formed in a tubular shape along a longitudinal axis between the distal end and the proximal end;
a reinforcing material made of metal that extends spirally around the longitudinal axis of the main body between the distal end and the proximal end of the main body and is embedded between an inner circumferential surface of the main body and an outer circumferential surface of the main body; and
a rib that is fixed to the outer circumferential surface of the main body along an entirety of a length of the rib along the longitudinal axis,
wherein the reinforcing material includes
a first portion spirally wound at a pitch that is substantially uniform,
a second portion that is connected to the first portion, and is spirally wound at a pitch larger than the pitch of the first portion, the pitch of the second portion being substantially uniform, and
a third portion that is connected to the second portion, and is spirally wound at a pitch larger than the pitch of the second portion.

10. The medical stent according to claim 9, further comprising:
a flap including a fixed end fixed to a proximal end side of the main body and a free end positioned outward of the outer circumferential surface of the main body in a radial direction of the main body, the flap extending from the fixed end to the free end,
wherein the rib is connected to the fixed end and at least partially extends linearly along the longitudinal axis from the fixed end toward the proximal end of the main body.

11. The medical stent according to claim 10, wherein
a volume per unit length of the rib is smaller than a volume per unit length of the flap, and
the rib is positioned closer to the proximal end of the main body than a boundary between the second portion and the third portion.

12. The medical stent according to claim 9, wherein
the main body further includes a resin inner layer and a resin outer layer, and
the reinforcing material is embedded between the resin inner layer and the resin outer layer.

13. The medical stent according to claim 9, further comprising:
a flap including a fixed end fixed to a proximal end side of the main body and a free end positioned outward of the outer circumferential surface of the main body in a radial direction of the main body, the flap extending from the fixed end to the free end,
wherein the rib is connected to the fixed end and extends along the longitudinal axis from the fixed end towards the proximal end of the main body.

14. A stent delivery device comprising:
a guide catheter including
a guide tube through which a guide wire can be inserted, and
a wire connected to the guide tube;
a pusher catheter including a first tube having a first lumen through which the wire can be inserted, and a second tube having a second lumen connected to a distal end of the first lumen and through which the guide tube can be inserted;

a connecting member including a loop that is connected to a distal end of the pusher catheter; and a stent configured to be attached to an outer circumferential surface of the guide tube and positioned distal of a distal end of the second tube, wherein the stent includes a resin main body that includes a distal end and a proximal end and is formed in a tubular shape along a longitudinal axis between the distal end and the proximal end, and a reinforcing material made of metal that extends spirally around the longitudinal axis of the main body between the distal end and the proximal end of the main body and is embedded between an inner circumferential surface of the main body and an outer circumferential surface of the main body, the reinforcing material including a first portion that is spirally wound, a second portion that is connected to the first portion, and is spirally wound at a pitch larger than a pitch of the first portion, and a third portion that is connected to the second portion, and is spirally wound at a pitch larger than the pitch of the second portion, the main body has a through hole that opens on the outer circumferential surface, and the stent is configured to be positioned with respect to the pusher catheter by inserting the guide tube into the loop of the connecting member in a state in which the loop is inserted into the through hole in the main body of the stent.

15. The stent delivery device according to claim 14, wherein the stent is configured to be detached from the guide tube by retracting the guide tube in a proximal direction relative to the stent such that the guide tube is retracted out of the stent and out of the loop of the connecting member.

16. The stent delivery device according to claim 14, wherein the stent further includes:

a first flap including a first fixed end fixed to a distal end side of the main body and a first free end positioned outward of the outer circumferential surface of the main body in a radial direction of the main body, the first flap extending from the first fixed end to the first free end, and a second flap including a second fixed end fixed to a proximal end side of the main body and a second free end positioned outward of the outer circumferential surface of the main body in the radial direction of the main body, the second flap extending from the second fixed end to the second free end.

17. The stent delivery device according to claim 16, wherein:

the second portion is positioned between the first fixed end and the second fixed end, and is spirally wound toward the second fixed end, the third portion is positioned between the proximal end of the main body and the second fixed end, and the through hole of the main body opens on the outer circumferential surface between the proximal end and the second fixed end.

\* \* \* \* \*